(12) United States Patent
Bosy et al.

(10) Patent No.: US 11,745,177 B2
(45) Date of Patent: Sep. 5, 2023

(54) ULTRASOUND LYSING OF WHOLE BLOOD

(71) Applicant: Instrumentation Laboratory Company, Bedford, MA (US)

(72) Inventors: Brian Joseph Bosy, Hull, MA (US); Josef Kerimo, Concord, MA (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 88 days.

(21) Appl. No.: 16/738,915

(22) Filed: Jan. 9, 2020

(65) Prior Publication Data

US 2020/0222894 A1 Jul. 16, 2020

Related U.S. Application Data

(60) Provisional application No. 62/790,520, filed on Jan. 10, 2019.

(51) Int. Cl.
*B01L 3/00* (2006.01)
*G01N 1/28* (2006.01)
(Continued)

(52) U.S. Cl.
CPC ............... *B01L 3/502* (2013.01); *G01N 1/28* (2013.01); *G01N 21/31* (2013.01); *G01N 33/721* (2013.01);
(Continued)

(58) Field of Classification Search
CPC .. B01L 3/502; B01L 2200/04; B01L 2300/06; B01L 2300/08; B01L 2300/12;
(Continued)

(56) References Cited

U.S. PATENT DOCUMENTS 5,141,718 A * 8/1992 Clark ..................... C12M 23/12
435/297.5
9,097,702 B2 8/2015 Fischbach
(Continued)

FOREIGN PATENT DOCUMENTS

EP 1181098 B2 2/2002
WO 00/72970 A1 12/2000

OTHER PUBLICATIONS

International Search Report and Written Opinion issued in corresponding PCT application No. PCT/US2020/012863, dated Apr. 1, 2020 (No. of pages 14).
(Continued)

*Primary Examiner* — Matthew D Krcha
*Assistant Examiner* — Jacqueline Brazin
(74) *Attorney, Agent, or Firm* — Burns & Levinson LLP

(57) ABSTRACT

A system and method for lysing of whole blood for CO-Ox measurement uses a lysing chamber for acoustic lysing of whole blood in a module in which the lysing chamber is separate from a CO-Ox measurement chamber. The disclosed acoustic lysing system and method avoids the expense and complexity of chemical lysing methods and allows the whole blood sample to be lysed while under continuous flow through the lysing chamber. The acoustic lysing chamber is provided upstream from a CO-Ox measurement chamber. The separation of the lysing chamber
(Continued)

from the Co-Ox measurement chamber provides freedom to arrange and orient various optical components and/or other CO-Ox measuring components around the CO-Ox measurement chamber. The decoupling of the lysing chamber from the CO-Ox measurement chamber allows for more efficient design of the ultrasonic lysing transducer and CO-Ox measurement optics.

20 Claims, 7 Drawing Sheets

(51) Int. Cl.
 *G01N 21/31* (2006.01)
 *G01N 33/72* (2006.01)
(52) U.S. Cl.
 CPC ....... *B01L 2200/04* (2013.01); *B01L 2300/06* (2013.01); *B01L 2300/08* (2013.01); *B01L 2300/12* (2013.01)
(58) Field of Classification Search
 CPC ....... B01L 2200/025; B01L 2300/0851; B01L 2300/087; B01L 2300/0877; B01L 3/502715; G01N 1/28; G01N 21/31; G01N 33/721; G01N 33/4925
 USPC .......................................................... 436/66
 See application file for complete search history.

(56) References Cited

U.S. PATENT DOCUMENTS

| | | | |
|---|---|---|---|
| 2002/0042125 A1 | 4/2002 | Petersen et al. | |
| 2003/0066915 A1* | 4/2003 | Taylor | C12M 47/06 241/100 |
| 2010/0151512 A1 | 6/2010 | Huemer | |
| 2016/0216284 A1* | 7/2016 | Misener | B01L 3/502715 |

OTHER PUBLICATIONS

International Preliminary Report on Patentability and Written Opinion dated Jul. 22, 2021, International Application No. PCT/US2020/012863 (8 pgs.).
First Office Action for Chinese Patent Application No. 202080012372.X, dated May 10, 2022, (with English translation), 16 pages.
Second Office Action for Chinese Patent Application No. 202080012372.X, dated Dec. 15, 2022, (with English translation), 13 pages.
Office Action in Chinese Application No. 202080012372.X dated Jun. 12, 2023, with English translation (10 pages).

* cited by examiner ns
ULTRASOUND LYSING OF WHOLE BLOOD

CROSS REFERENCE TO RELATED APPLICATIONS

This application claims priority to U.S. provisional patent application No. 62/790,520 entitled "Ultrasound Lysing of Whole Blood" which was filed on Jan. 10, 2019 and which is incorporated by reference herein in its entirety.

BACKGROUND

Some currently used CO-oximetry (CO-Ox) measurement instruments implement chemical lysing techniques to lyse whole blood prior to performing CO-Ox measurement. Such chemical lysing techniques generally involve complicated fluidic processes and numerous dedicated components for handling reagents, metering, mixing, and controlling valves, for example.

As an alternative to chemical lysing of whole blood, some previously known CO-Ox measurement techniques use acoustic waves to lyse whole blood. For example, U.S. Pat. No. 9,097,702 and U.S. Patent Application Publication No. 2010/0151512 describe systems that use acoustic waves to lyse whole blood. These previously known designs are based on a coaxial configuration where the lysing and CO-Ox chambers serve the same purpose and lysing occurs directly over a CO-Ox cell. In this configuration, whole blood fills the CO-Ox measurement and lysing chamber wherein the whole blood is then acoustically lysed. The chamber is typically about 0.09 mm to 0.12 mm in depth for CO-Ox measurement. However, as blood is moved through such a small space, clots present in whole blood can be trapped in the chamber. Furthermore, the coaxial configuration used in both of these previously known techniques also restrains the designs of both the CO-Ox optics and the ultrasound transducer making their design far from optimal.

SUMMARY

The apparatus for analyzing blood according to an aspect of the present disclosure includes a cartridge configured for removable installation in a blood analyzing instrument, wherein the cartridge includes a lysing chamber configured for receiving a whole blood sample and a separate CO-Ox measurement chamber downstream from the lysing chamber. According to the an aspect of the present disclosure, the lysing chamber includes at least one interface surface configured for transmitting ultrasonic energy from an ultrasonic transducer of the blood analyzing instrument to the blood sample for performing lysing of the blood sample.

The CO-Ox measurement chamber is separate from the lysing chamber and is configured for receiving the blood sample from the lysing chamber subsequent to lysing of the blood sample. The measurement chamber is configured to facilitate performing a CO-Ox measurement of the blood sample by the blood analyzing instrument.

DETAILED DESCRIPTION

According to an aspect of the present disclosure, an ultrasonic lysing chamber is used to lyse whole blood for CO-Ox measurement. The ultrasonic lysing chamber and techniques for lysing blood for measuring CO-Ox disclosed herein avoid the expense and complexity of chemical lysing methods used in some existing CO-Ox measuring instruments. A system and method for lysing of whole blood for CO-Ox measurement according to an aspect of the present disclosure uses a lysing chamber for acoustic lysing of whole blood in a module in which the lysing chamber is separate from a CO-Ox measurement chamber. The lysing chamber is provided upstream from the CO-Ox measurement chamber. The separation of the lysing chamber from the Co-Ox measurement chamber according to the present disclosure overcomes some of the disadvantages of previously known ultrasonic lysing techniques The disclosed system and apparatus provides freedom to arrange and orient various optical components and/or other CO-Ox measuring components around the CO-Ox measurement chamber, for example. The decoupling of the lysing chamber from the CO-Ox measurement chamber allows for more efficient design of the ultrasonic lysing transducer and CO-Ox measurement optics. The disclosed separate lysing chamber can be much larger than previously the lysing chambers of previous apparatus which served a dual purpose as CO-Ox measurement chambers because the disclosed lysing chamber is not limited to configurations suitable for CO-Ox measurement. In an illustrative embodiment, the disclosed lysing chamber is about 0.23 mm in depth. This much larger lysing chamber depth, compared to the 0.09 mm to 0.12 mm depth of the previously known lysing and CO-Ox chambers for example, substantially reduces the trapping of clots. Furthermore, clots present in whole blood can be broken up in the disclosed lysing chamber by the ultrasound lysing process to prevent them from getting trapped downstream in the more restrictive CO-Ox chamber.

Another benefit of the disclosed method and apparatus is that it facilitates the lysing of whole blood using much less power than previously known techniques such that the thermal impact of ultrasonic lysing on the blood sample is minimized. According to another aspect of the present disclosure, the lysing of whole blood is performed more efficiently than in previously known techniques, because the disclosed method and apparatus allows the whole blood sample to be lysed while under continuous flow through the lysing chamber.

Figure 1:
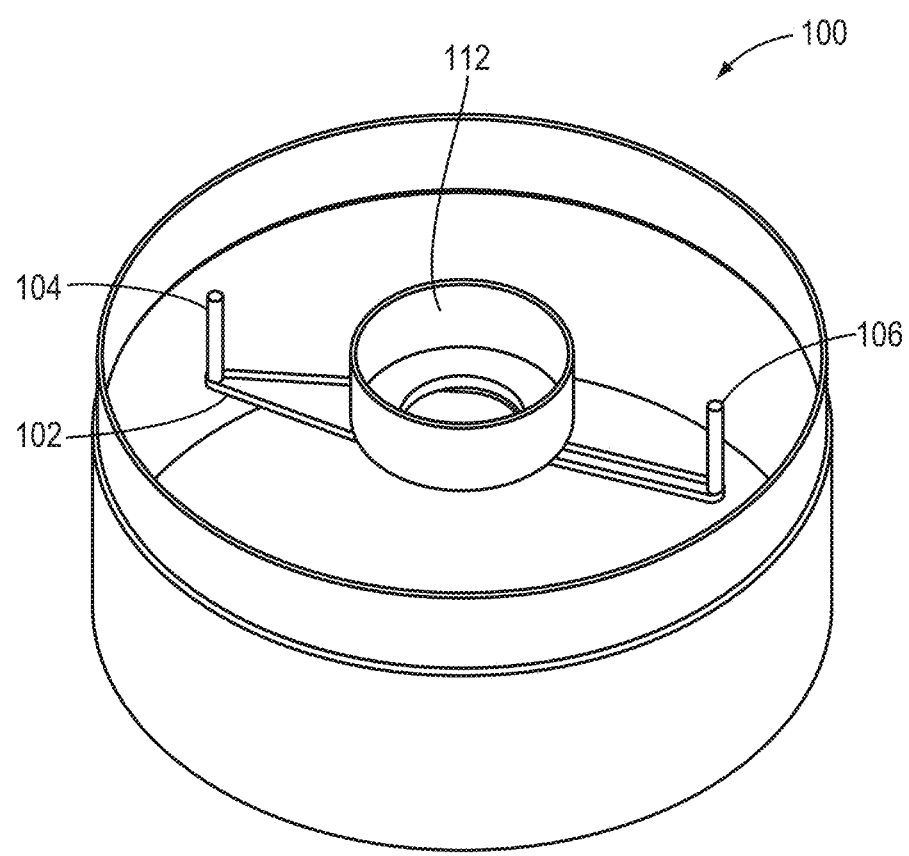
FIG. 1 illustrates a module including a lysing chamber according to an aspect of the present disclosure

Referring to FIG. 1, an illustrative embodiment of a module 100 including the disclosed lysing chamber 102 is made from a molded disposable plastic material suitable for repeatably receiving ultrasound energy. The lysing chamber 102 has a depth dimension sufficiently large enough to avoid clogging by clots present in whole blood. The module includes a blood inlet port 104 in communication with the lysing chamber 102 and a lysed blood outlet port providing 106 a fluid path between the lysing chamber 102 and a measurement chamber.

Figure 2:
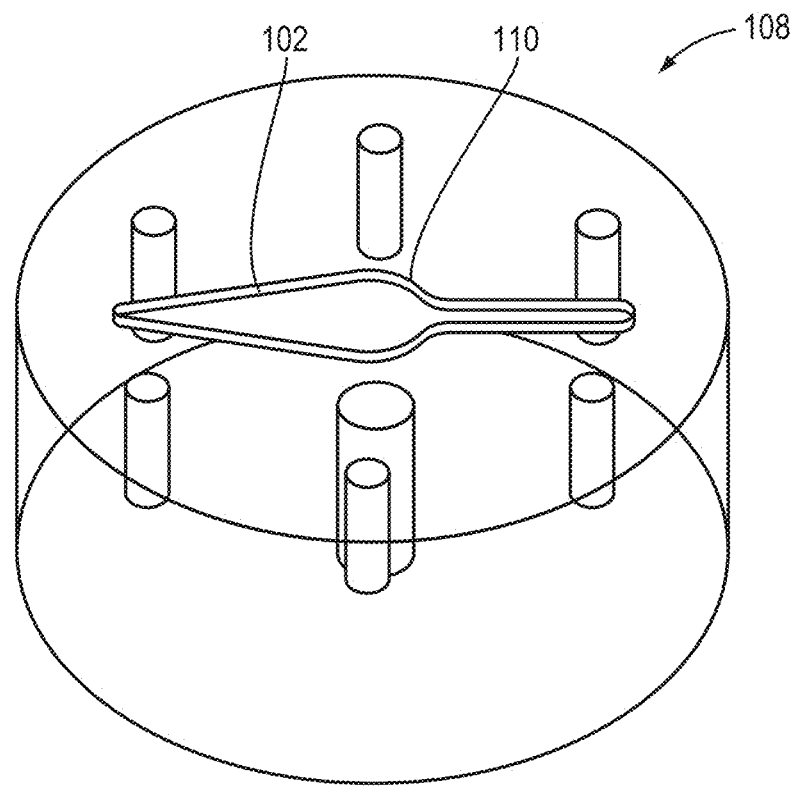
FIG. 2 illustrates a bottom portion a module according to an aspect of the present disclosure in which the lysing chamber has a tear-shaped geometry.

FIG. 2 shows a bottom portion 108 of the module 100 to show an illustrative embodiment in which the lysing chamber 102 has a tear-shaped geometry, which gradually expands toward a circular region 110, wherein the ultrasonic energy is transmitted to lyse the whole blood in the circular region.

Figure 3:
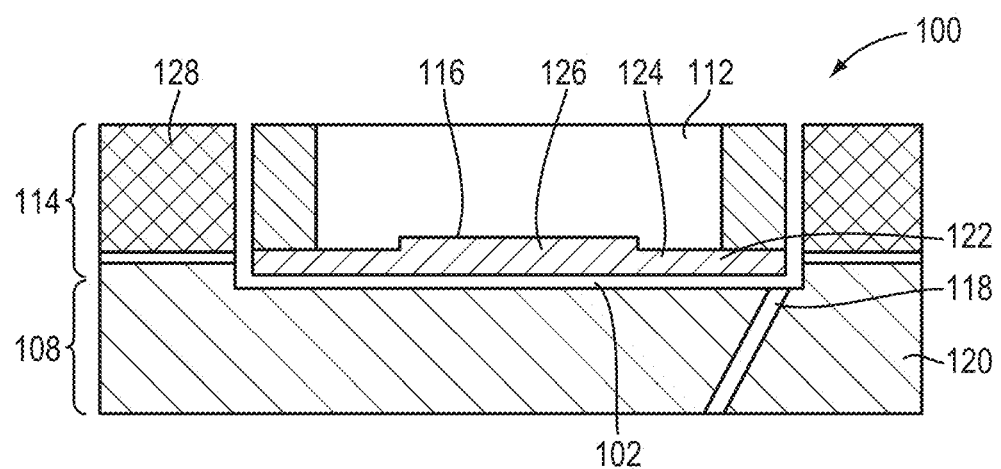
FIG. 3 is a cross sectional view showing a bottom portion of a module and a top portion of the module according to an aspect of the present disclosure.

FIG. 3 is a cross sectional view of the module 100 showing the bottom portion 108 of the module 100 and a top portion 114 of the module 100. According to an aspect of the present disclosure, the module 100 also includes a recess 112 configured for receiving an ultrasonic transducer and locating the ultrasonic transducer against an interface surface 116 of the module 110. The lysing chamber 102 has a bottom wall 118 formed in the bottom portion 108 of the module 100. In an illustrative embodiment, the module 100 may include a first webbed portion 120 below the bottom wall 118 of the lysing chamber 102.

A top wall 122 of the lysing chamber is configured to vibrate in response to receiving energy from the ultrasonic transducer. In an illustrative embodiment, the top wall 122 includes a thin portion 124 and a protruding central disk portion 126. In an illustrative embodiment, the thin portion has a thickness dimension of about 0.5 mm. The central disk portion 126 is located over the circular region 110 of the lysing chamber 102. The central disk portion 126 the may be a separate piece attached to the top wall 122 of the lysing chamber 102 or it may be formed integrally with the top wall 122, for example. The interface surface 116 of the module 100 comprises the top surface of the central disk portion 126.

According to an aspect of the present disclosure, the ultrasonic transducer is separate from the module 100. The ultrasonic transducer can be placed directly against the interface surface 116. The disclosed method and apparatus can allow a wide tolerance of location between the ultrasonic transducer and the interface surface 116 by spring loading the ultrasonic transducer, for example. The interface surface 116 is vibrated by the ultrasonic transducer to facilitate the transmission of ultrasonic energy from the ultrasonic transducer to the blood sample. In an illustrative embodiment, the ultrasonic transducer vibrates at 40 kilohertz with a power level of about 30 watts.

The module 100 includes a second webbed portion 128 which provides a connection between the lysing chamber and the ultrasonic transducer. The second webbed portion 128 aids in transmission of ultrasonic waves from the ultrasonic transducer to the blood sample without requiring any coupling fluid to achieve efficient transmission of the ultrasonic energy directly into the blood.

In an illustrative embodiment, the module is designed to be placed inside an automated blood analysis instrument such as the next generation GEM blood analysis instrument, by Instrumentation Laboratories of Bedford, Mass. The lysing chamber module 100 is installed in or incorporated in a removable cartridge that is configured to be removably installed in the blood analysis instrument. When the cartridge is installed in the blood analysis instrument, the recess and central disk portion of the module are aligned with an ultrasonic transducer. The ultrasonic transducer is incorporated in the blood analysis instrument.

According to an aspect of the present disclosure, the lysing chamber is disposable along with the removable cartridge and does not require a tight alignment with the ultrasonic transducer. According to another aspect of the present disclosure, the lysing chamber is kinematically aligned with an insertion direction of the cartridge with respect to the blood analyzing instrument.

Figure 4:
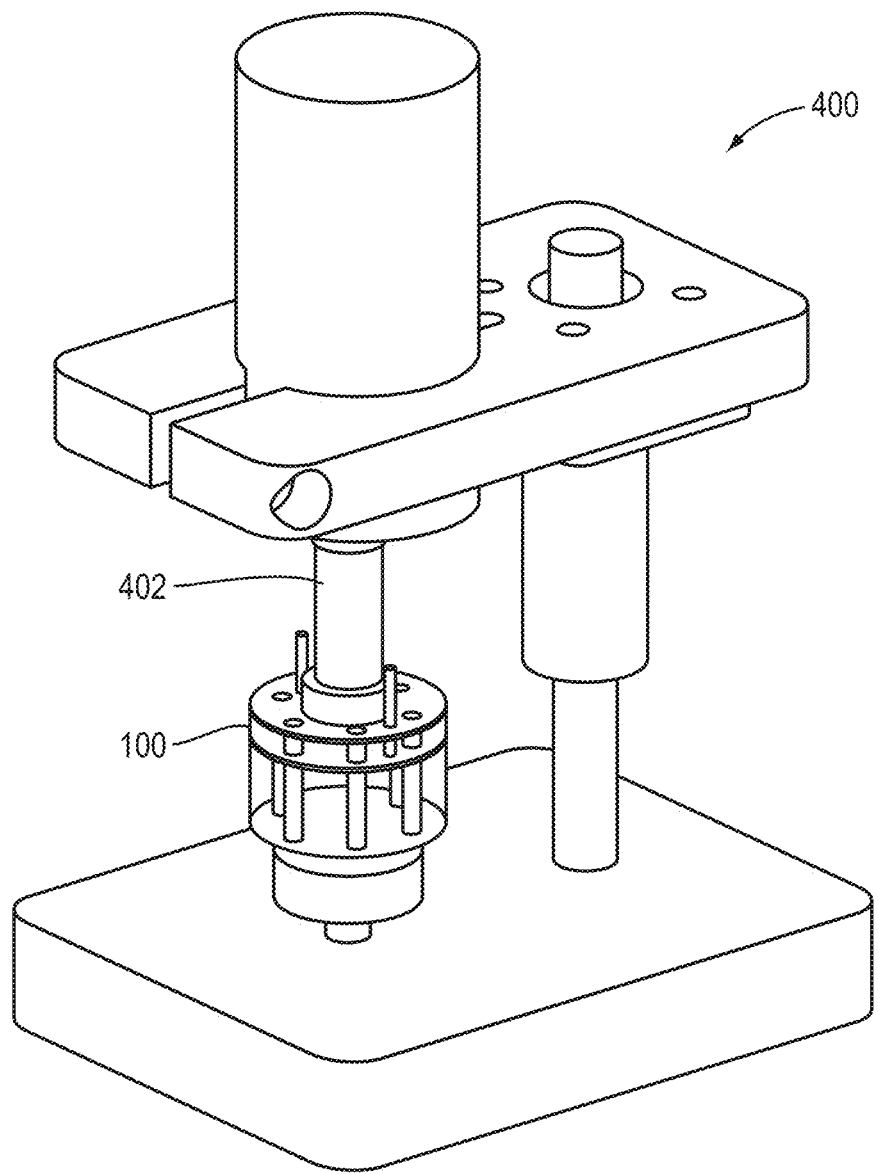
FIG. 4 illustrates a test apparatus in which an ultrasonic transducer is configured against a module according to an aspect of the present disclosure.

FIG. 4 shows a test apparatus 400 in which an ultrasonic transducer 402 is configured against the disclosed module 100. Ultrasonic energy was applied to a whole blood sample using the configuration shown in FIG. 4 to demonstrate that the disclosed ultrasonic method and apparatus for lysing blood achieves CO-Ox measurement results that are similar to CO-Ox measurement results of chemical lysed blood.

Figure 5:
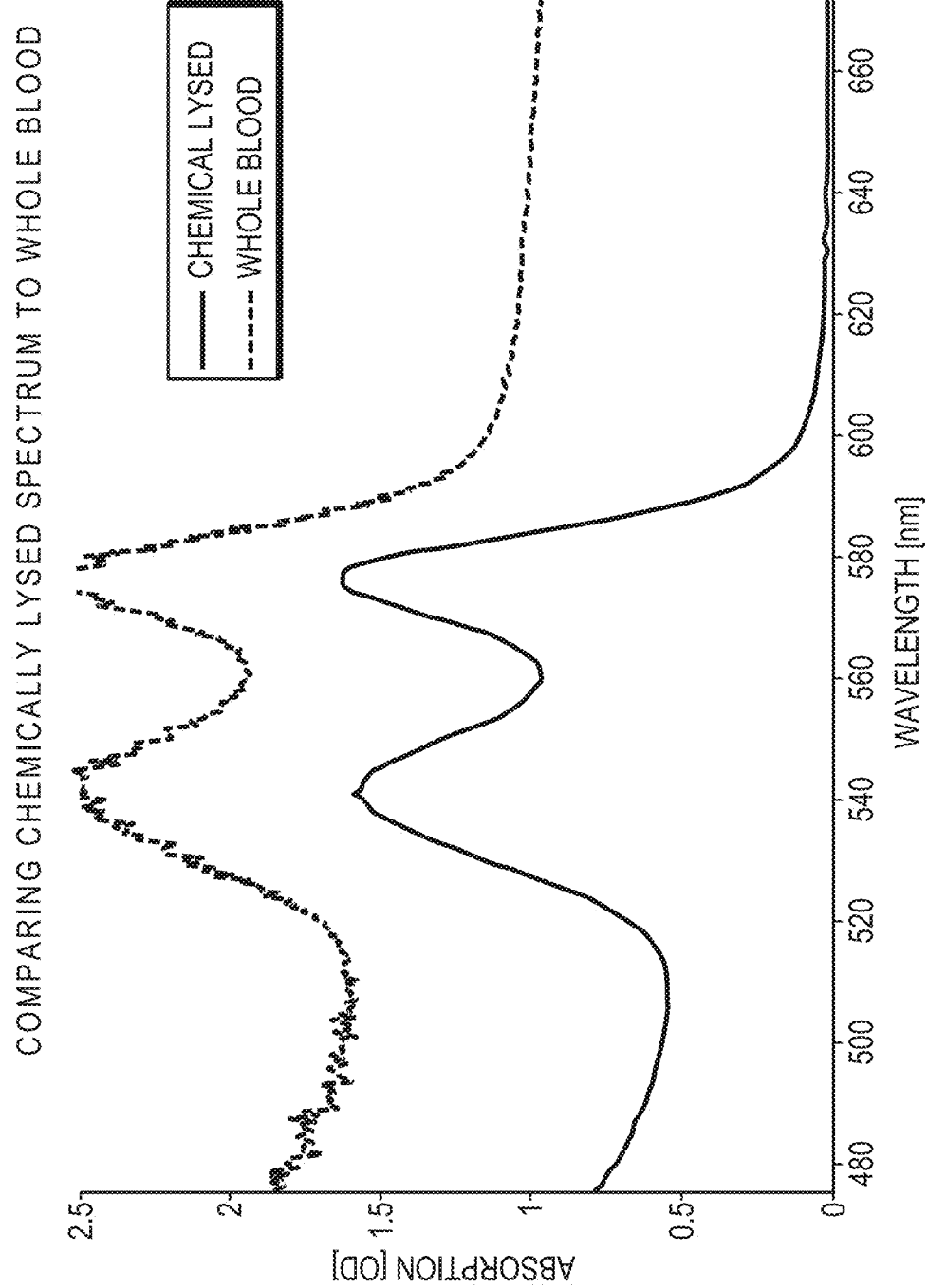
FIG. 5 is a graph showing an absorption spectrum of whole blood that has not been lysed compared to an absorption spectrum of blood that has been chemically lysed according to an aspect of the present disclosure.
Figure 6:
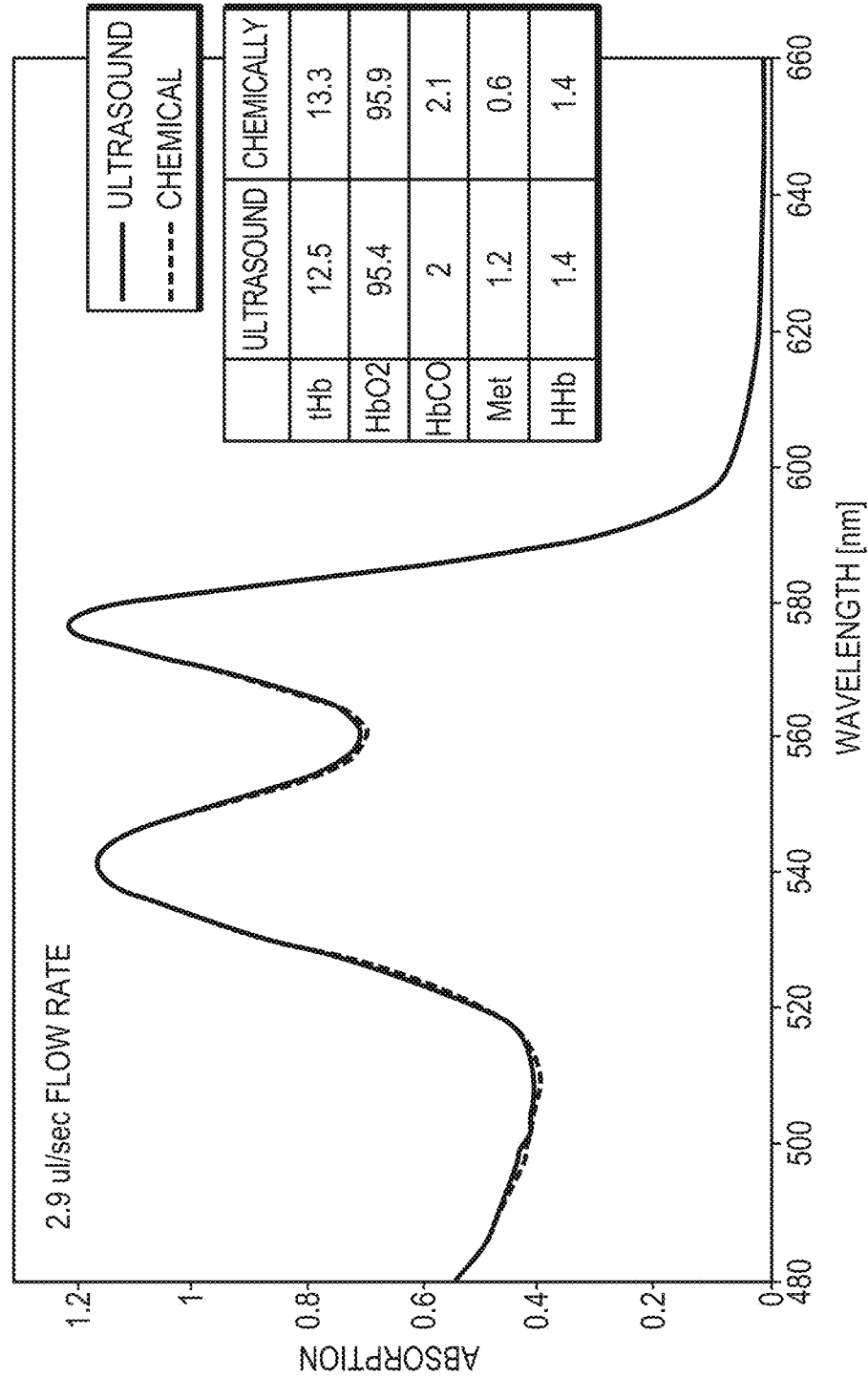
FIG. 6 is a graph showing absorption spectra of blood that has been lysed with an apparatus according to an aspect of the present disclosure and blood that has been chemically lysed.
Figure 7:
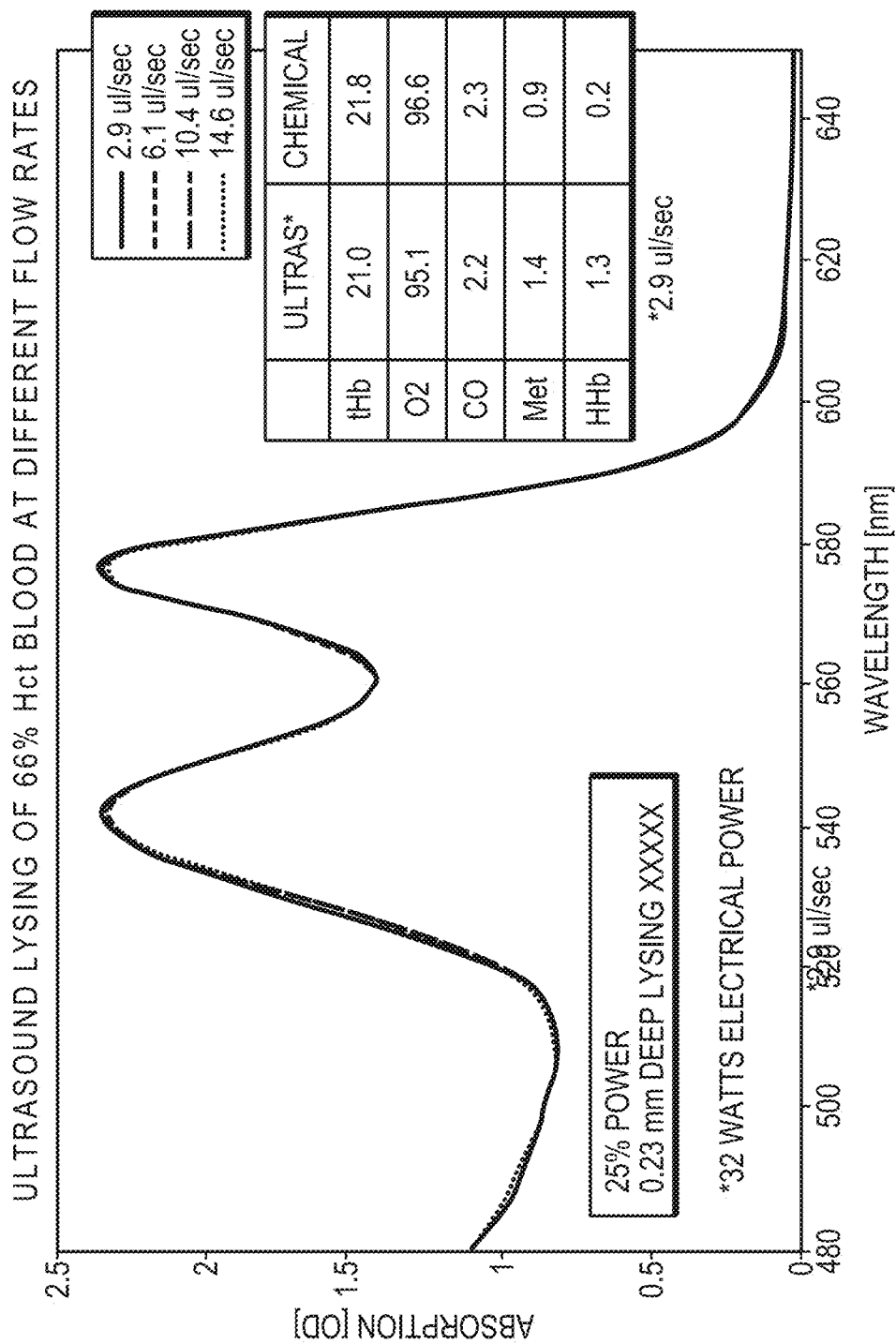
FIG. 7 is a graph showing absorption spectra of whole blood from the same donor (66% Hct) lysed with different flow rates according to an aspect of the present disclosure.

FIG. 5 is a graph showing an absorption spectrum of whole blood that has not been lysed compared to an absorption spectrum of blood that has been chemically lysed. The absorption spectra in FIG. 5 was measured using the optics of a GEM 4K blood analysis instrument by Instrumentation Laboratories of Bedford, Mass. FIGS. 6 and 7 show that lysing of whole blood using the ultrasonic lysing methods and apparatus disclosed herein before performing CO-Ox measurement of the ultrasonically lysed blood results in a CO-Ox spectrum comparable to that of chemically lysed blood with similar properties.

FIG. 6 shows absorption spectra of blood that has been lysed with the apparatus of the present invention and that has been chemically lysed. The sample was under constant flow rate while filling the lysing chamber (2.9 µl/sec). The two lysed samples where then analyzed on the GEM 4K instrument to see the effect on the hemoglobin measurements. The different fractions of hemoglobin are listed on the inset for both chemically and ultrasound lysed blood.

FIG. 7 shows absorption spectra of whole blood from the same donor (66% Hct) lysed with different flow rates and 32 Watts. The inset shows the different hemoglobin fractions as measured with a GEM 4K instrument. The flow rates tested are well below and above the rates used on the current GEM 5K blood analysis instrument by Instrumentation Laboratories of Bedford, Mass.

FIGS. 6 and 7 show that whole blood is lysed very efficiently with the apparatus and methods disclosed herein and that the apparatus and methods disclosed herein can be used with the existing CO-Ox optics and algorithms.

Figure 8:
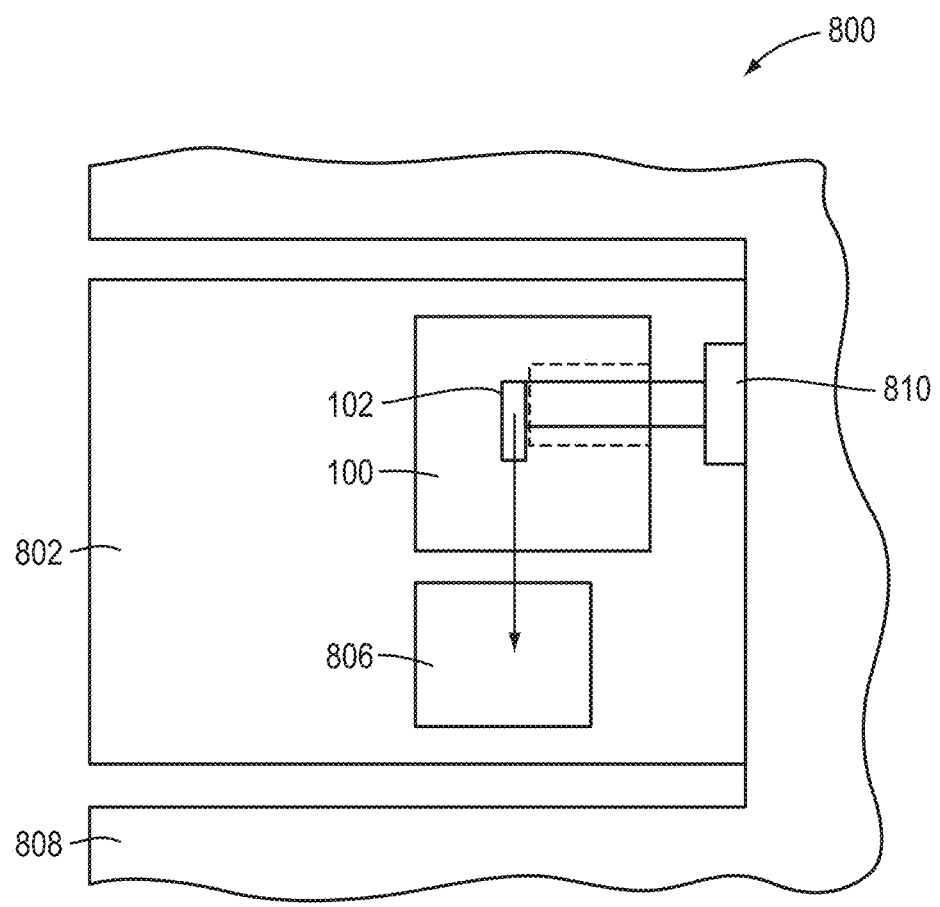
FIG. 8 is a schematic dragging of an apparatus for analyzing blood according to an aspect of the present disclosure.

An apparatus for analyzing blood, according to an aspect of the present disclosure is described with reference to FIG. 8. In an illustrative embodiment, the apparatus 800 includes a cartridge 802 configured for removable installation in a blood analyzing instrument 808. The blood analyzing instrument 808 includes an ultrasonic transducer 810. The cartridge 802 includes a lysing chamber 102 and a measurement chamber 806 separate from the lysing chamber 102. The lysing chamber 102 is configured for receiving a blood sample and includes at least one interface surface configured for transmitting ultrasonic energy from the ultrasonic transducer 810 of the blood analyzing instrument 808 to the blood sample to performing lysing of the blood sample. The measurement chamber 806 is configured for receiving the blood sample from the lysing chamber 102 subsequent to the lysing. The measurement chamber 806 is also configured to facilitate performing a CO-Ox measurement of the blood sample by the blood analyzing instrument.

In an illustrative embodiment, the lysing chamber is made from a molded disposable plastic material suitable for repeatably receiving ultrasound energy. A depth dimension of the lysing chamber is sufficiently large to avoid clogging by clots present in whole blood. In an example embodiment, the depth dimension is about 0.23 millimeters. According to an aspect of the present disclosure, the lysing chamber is kinematically aligned with an insertion direction of the cartridge with respect to the blood analyzing instrument.

In an illustrative embodiment, the cartridge also includes a blood inlet port in communication with the lysing chamber. A recess in the cartridge is configured for receiving an ultrasonic transducer and retaining the ultrasonic transducer against the interface surface. In the illustrative embodiment, the cartridge also includes a lysed blood outlet port between the lysing chamber and the measurement chamber. According to another aspect of the present disclosure the lysing chamber has a tear-shaped geometry that gradually expands toward a circular region. The ultrasound energy is transmitted to lyse the whole blood in the circular region.

In an illustrative embodiment, the ultrasonic transducer generates ultrasonic energy in a frequency range of 20 kHz to 60 kHz. For example, in a particular embodiment the ultrasonic transducer generates ultrasonic energy at a frequency of about 40 kHz.

According to another aspect of the present disclosure, the apparatus 800 also includes a central vibrated disk attached to the lysing chamber body adjacent the interface surface. The central vibrated disk is configured to facilitate transmission of the ultrasonic energy to the blood sample. According to another aspect of the present disclosure, the cartridge further comprises a web shaped portion between the lysing chamber and the ultrasonic transducer. According to another aspect of the present disclosure, the lysing is performable under a continuous flow of the blood sample through the lysing chamber.

What is claimed is:

1. An apparatus comprising:
    a cartridge configured for removable installation in a blood analyzing instrument, the cartridge comprising:
        a lysing chamber configured to receive a blood sample, the lysing chamber comprising a wall, the wall comprising a first part and a second part that surrounds the first part, the first part being thicker than the second part, and the first part comprising at least one interface surface configured to contact an ultrasonic transducer of the blood analyzing instrument and to transmit ultrasonic energy from the ultrasonic transducer to the blood sample to lyse the blood sample and thereby produce a lysed blood sample; and
        a measurement chamber separate from the lysing chamber, the measurement chamber being configured to receive the lysed blood sample from the lysing chamber, and the measurement chamber being configured to enable performing a CO-Ox (CO-oximetry) measurement of the lysed blood sample by the blood analyzing instrument;
    wherein the lysing chamber has a tear-shaped geometry, the tear-shaped geometry gradually expanding toward a substantially circular region, the first part being over the substantially circular region and the ultrasonic energy being transmitted to lyse the blood sample in the substantially circular region.

2. The apparatus of claim 1, wherein the lysing chamber comprises a molded disposable plastic material configured for repeatably receiving ultrasound energy.

3. The apparatus of claim 1, wherein a depth dimension of the lysing chamber is sufficiently large to avoid clogging by blood clots.

4. The apparatus of claim 3, wherein the depth dimension is about 0.23 millimeters.

5. The apparatus of claim 1, wherein the lysing chamber is aligned with an insertion direction of the cartridge into the blood analyzing instrument.

6. The apparatus of claim 1, wherein the cartridge further comprises:
    a blood inlet port in communication with the lysing chamber;
    a recess configured for receiving the ultrasonic transducer and for retaining the ultrasonic transducer against the at least one interface surface; and
    a lysed blood outlet port between the lysing chamber and the measurement chamber.

7. The apparatus of claim 1, wherein the ultrasonic energy is in a frequency range of 20 kHz to 60 kHz.

8. The apparatus of claim 1, wherein the ultrasonic energy is at a frequency of about 40 kHz.

9. The apparatus of 1, wherein the first part comprises a central disk.

10. The apparatus of claim 1, wherein the cartridge further comprises a web shaped portion among the lysing chamber and the ultrasonic transducer.

11. The apparatus of claim 1, wherein lysing is performable under a continuous flow of the blood sample through the lysing chamber.

12. A method for performing a CO-Ox (CO-oximetry) measurement of ultrasonically-lysed blood, the method comprising:
    directing a blood sample to a lysing chamber of a cartridge configured for removable installation in a blood analyzing instrument;
    applying ultrasonic energy from an ultrasonic transducer to a wall of the lysing chamber, the wall comprising a first part and a second part that surrounds the first part, the first part being thicker than the second part, and the first part comprising at least one interface surface, the at least one interface surface contacting an ultrasonic transducer of the blood analyzing instrument and transmitting the ultrasonic energy to the blood sample to lyse the blood sample and thereby produce the ultrasonically-lysed blood, the lysing chamber having a tear-shaped geometry, the tear-shaped geometry gradually expanding toward a substantially circular region, the first part being over the substantially circular region and the ultrasonic energy being transmitted to lyse the blood sample in the substantially circular region;
    directing the ultrasonically-lysed blood out of the lysing chamber to a separate measurement chamber of the cartridge; and
    performing the CO-Ox measurement of the ultrasonically-lysed blood in the measurement chamber using the blood analyzing instrument.

13. The method of claim 12, wherein applying the ultrasonic energy is performed during flow of the blood sample through the lysing chamber.

14. The method of claim 12, wherein the lysing chamber comprises a molded disposable plastic material configured for repeatably receiving ultrasound energy.

15. The method of claim 12, wherein a depth dimension of the lysing chamber is sufficiently large to avoid clogging by blood clots.

16. The method of claim 12, wherein the ultrasonic energy is in a frequency range of 20 kHz to 60 kHz.

17. The method of claim 12, wherein the lysing chamber is aligned with an insertion direction of the cartridge containing the lysing chamber into the blood analyzing instrument.

18. The method of claim 17, wherein the cartridge comprises:
   a blood inlet port in communication with the lysing chamber;
   a recess configured for receiving the ultrasonic transducer and for retaining the ultrasonic transducer against the at least one interface surface; and
   a lysed blood outlet port between the lysing chamber and the measurement chamber.

19. The apparatus of claim 1, wherein a dimension of the lysing chamber is sufficiently large to avoid clogging by blood clots.

20. The method of claim 12, wherein a dimension of the lysing chamber is sufficiently large to avoid clogging by blood clots.

\* \* \* \* \*